United States Patent [19]

Kurihara et al.

[11] Patent Number: 4,990,337

[45] Date of Patent: Feb. 5, 1991

[54] CYCLOSPORIN FORMULATIONS OF MONO OR DIGLYCERIDE FATTY ACID

[75] Inventors: Kozo Kurihara; Masaru Murano, both of Tokyo, Japan

[73] Assignee: Sankyo Company Limited, Tokyo, Japan

[21] Appl. No.: 511,992

[22] Filed: Apr. 12, 1990

Related U.S. Application Data

[63] Continuation of Ser. No. 303,646, Jan. 27, 1989, abandoned.

[30] Foreign Application Priority Data

| Jan. 29, 1988 | [JP] | Japan | 63-19125 |
| May 10, 1988 | [JP] | Japan | 63-111639 |
| Jul. 22, 1988 | [JP] | Japan | 63-183127 |

[51] Int. Cl.$^5$ ............................................. A61K 9/10
[52] U.S. Cl. .................................... 424/427; 424/428; 514/15; 514/786; 514/885; 514/914
[58] Field of Search ............... 424/427, 428; 514/15, 514/786, 885, 914

[56] References Cited

U.S. PATENT DOCUMENTS

| 2,865,859 | 12/1958 | Lubowe | 514/885 X |
| 3,678,149 | 7/1972 | Prigal | 514/885 X |
| 4,388,307 | 6/1983 | Cavanak | 424/177 |
| 4,474,751 | 10/1984 | Haslam et al. | 514/912 X |
| 4,612,193 | 9/1986 | Gordon et al. | 514/914 X |
| 4,649,047 | 3/1987 | Kaswan | 514/912 |
| 4,659,696 | 4/1987 | Hirai et al. | 514/15 |
| 4,670,419 | 6/1987 | Uda et al. | 514/16 |
| 4,711,902 | 12/1987 | Serno | 514/356 |
| 4,722,914 | 2/1988 | Eckert et al. | 514/786 X |
| 4,839,342 | 6/1989 | Kaswan | 514/915 |

FOREIGN PATENT DOCUMENTS

| 897724 | 7/1983 | Belgium . | |
| 94157 | 11/1983 | European Pat. Off. . | |
| 0143305 | 6/1985 | European Pat. Off. . | |
| 0170623 | 2/1986 | European Pat. Off. . | |
| 149197 | 7/1985 | Fed. Rep. of Germany . | |
| 0641356 | 2/1984 | Switzerland | 424/177 |
| 2015339 | 9/1979 | United Kingdom . | |

*Primary Examiner*—Thurman K. Page
*Attorney, Agent, or Firm*—Frishauf, Holtz, Goodman & Woodward

[57] ABSTRACT

Cyclosporins are useful immunosuppressive, anti-fungal and antiphlogistic agents which are relatively insoluble in water and aqueous fluids (including body fluids). They may be rendered more soluble or dispersible in aqueous media by first dissolving them in at least one mono- or di- glyceride of a $C_6$–$C_{10}$ fatty acid, and the resulting solution can then easily be emulsified in water or an aqueous fluid.

58 Claims, No Drawings

CYCLOSPORIN FORMULATIONS OF MONO OR DIGLYCERIDE FATTY ACID

This application is a continuation of application Ser. No. 07/303,646, filed Jan. 27, 1989, now abandoned.

BACKGROUND TO THE INVENTION

The present invention relates to a novel pharmaceutical composition wherein at least one cyclosporin, which is the active ingredient, is accompanied by a solubilising agent which is a mono- or di- glyceride of an intermediate molecular weight fatty acid (i.e. a fatty acid having from 6 to 10 carbon atoms).

The cyclosporins are a homologous group of biologically active oligopeptides, which are metabolites produced by certain fungi imperfecti. Cyclosporin A is the best known member of this group, but cyclosporins B to I have also so far been identified, and the commercially available product may contain a mixture of several individual cyclosporins. They all share a cyclic peptide structure consisting of 11 amino acid residues with a total molecular weight of about 1,200, but with different substituents or configuration of some of the amino acids [Merck Index, 2748, 10th Ed.; Helv. Chim. Acta 60, 1568–1578 (1977); Helv, Chim. Acta 65, 1655–1677 (1982)].

For convenience, the term "cyclosporin" (in the singular and without further qualification) will be used hereinafter to designate the cyclosporin component of the composition of the present invention. However, it should be understood that, as used with reference to the invention, this term is intended to include any individual member of the cyclosporin group, as well as mixtures of two or more such individual cyclosporins whether of two or more such individual cyclosporins whether in the form of commercially available mixtures or otherwise.

Cyclosporin has immunosuppressive, antifungal and antiphlogistic activities, but has so far been primarily used therapeutically for its immunosuppressive activity. In its therapeutic use as an immunosuppressive, it is currently used either orally or by injection. However, since the solubility of cyclosporin in water is extremely low (e.g 20 $\mu$g/ml to 30 $\mu$g/ml for cyclosporin A), both types of formulation are prepared as an oily solution containing ethanol. Even so, the bioavailability of its oral preparations is extremely low, generally below 30% [K. Takada et al. Drug Delivery System 1, No. 1, 1–7 (1986)]. This is believed to be due to the separation of cyclosporin as a solid immediately after it comes into contact with water, e.g. in the mouth or in the gut. Injectable preparations of cyclosporin formed as an oily solution containing ethanol have first to be diluted with physiological saline before intravenous administration. In the case of intravenous administration, however, it is clearly not merely undesirable but highly dangerous for cyclosporin to separate out on contact with water. Accordingly, a surface active agent, such as a polyoxyethylated castor oil, is added as a solubilizer to injectable preparations in order to prevent the cyclosporin from separating out. However, the addition of surface active agents, such as polyoxyethylated castor oil, to injectable preparations can give rise to safety problems.

Cyclosporin is effective in the treatment of the ocular symptoms of Behcet's Syndrome. When it is administered orally for the treatment of these symptoms and relies upon systemic circulation to reach the eyes, the side effects of the drug may cause various adverse reactions, such as hypertrichosis or renal dysfunction. However, when oily preparations containing cyclosporin are applied directly to the eyes, irritation or a clouded visual field may frequently result. Hence, cyclosporin is, in reality, of little practical use in the treatment of the ocular symptoms of Behcet's Syndrome, for which it would otherwise be very well suited. Moreover, if it were possible to prepare a formulation suitable for topical application to the eyes, it would be expected to have various other uses in addition to the treatment of the ocular symptoms of Behcet's Syndrome. For example, from its pharmacological mode of action, it is thought that it could be useful during keratoplasty as well as in the treatment of herpetic keratitis and spring catarrh.

One way of overcoming the problem of inadequate water solubility would be to dissolve sufficient cyclosporin in an aqueous solvent system so as to reach an effective concentration for treatment. Such a solvent system should not contain any additive, such as a surface active agent, which could give rise to safety problems. If this could be achieved, the cyclosporin would already be in an aqueous solution and its contact with bodily fluids would merely constitute dilution, so that it would not immediately separate out when contacted with the water of such fluids. However, so far it has been very difficult to make any such preparation because cyclosporin has an extremely low solubility in water and has a cyclic structure with a molecular weight significantly greater than 1,000, with the result that insufficient can be dissolved to be effective for the desired treatment. Table 1 shows the solubility of cyclosporin A in various kinds of solvents, from which it can be seen that the solubility pattern seems quite unique.

TABLE 1

| Solvent | Solubility parameters | | | Solubility of cyclosporin A [mg/ml] |
|---|---|---|---|---|
| | $\delta d$ | $\delta p$ | $\delta h$ | |
| Methanol | 7.4 | 6.0 | 10.9 | >1000 |
| Ethanol | 7.7 | 4.3 | 9.5 | >1000 |
| Acetonitrile | 7.5 | 8.8 | 3.0 | >1000 |
| Ethyl acetate | 7.4 | 2.6 | 4.5 | >1000 |
| Benzene | 8.9 | 0.5 | 1.0 | 400 |
| Tetrahydrofuran | 8.2 | 2.8 | 3.9 | 400 |
| Acetone | 7.6 | 5.1 | 3.4 | 100 |
| Propylene glycol | 8.2 | 4.6 | 11.4 | 100 |
| Isopropanol | 7.7 | 3.0 | 8.0 | 50 |
| Cyclohexane | 8.2 | 0.0 | 0.0 | 20 |
| Hexane | 7.2 | 0.0 | 0.0 | <10 |
| Water | 6.0 | 15.3 | 16.7 | <1 |

In the above Table, $\delta d$, $\delta p$ and $\delta h$ are measures of dispersion force, polarity and hydrogen bonding, respectively.

In view of these solubility properties, it has, in the past, been considered not merely difficult but practically impossible to design reasonably a pharmaceutical composition containing cyclosporin dissolved in an aqueous medium.

Although the cyclosporins have demonstrated some solubility in oily preparations containing higher fatty acid glycerides, such as olive oil, peanut oil and/or castor oil, these frequently produce an unpleasant sensation when applied to the eye because of stimulation or the viscousness which is characteristic of these oils.

We have previously proposed in USSN 201 579, filed 1st of June, 1988, to solubilise cyclosporin by using it in admixture with at least one α-cyclodextrin and/or derivative thereof; however, that previous proposal differs from the present invention in that it actually solubilises the active compound, whereas, in the present invention, the active compound is dissolved in a glyceride, which may then be emulsified in water.

It is known that intermediate molecular weight fatty acid triglycerides and higher fatty acid glycerides can be employed in cyclosporin compositions [see, for example, U.S. Pat. No. 4,388,307], but these glycerides are unsatisfactory for use as envisaged by the present invention, and this is demonstrated later herein.

In Belgian Pat. No. 895 724, there is disclosed the use of a derivative of the cyclosporins, namely dihydrocyclosporin D, in the treatment of multiple sclerosis, and, among many others, there are described gelatine capsules in which the dihydrocyclosporin D is dissolved in a non-aqueous mixture of ethanol, Imwitor (trade mark) 742 and Maisine. However this differs from the present invention in that there is no suggestion that the composition is or need be dissolved or dispersed in water. Furthermore, these compositions only attain solubility of the cyclosporin by the inclusion of additional cyclosporin solvents, in particular ethanol and (in the case of Example 1) the cyclosporin solubilising agent Labrafil 2152. Similar considerations also apply to other formulations comprising cyclosporins known from the art, e.g. as herein discussed.

We have now found that the cyclosporins have excellent solubility in the mono- and di- glycerides of intermediate molecular weight fatty acids, which are easily emulsified in water, and which can thus substantially improve the dispersibility of cyclosporin in water and aqueous media. It is considered that this is most surprising in view of the difficulties experienced with higher fatty acid glycerides and even with the triglycerides of intermediate molecular weight fatty acids.

BRIEF SUMMARY OF INVENTION

It is an object of the present invention to provide a pharmaceutical composition in which the cyclosporin is solubilised in a non-irritating base, which enables the cyclosporin to be dispersed with ease in water or aqueous media, for example bodily fluids.

Thus, in accordance with the present invention, there is provided, as a new composition of matter, a pharmaceutical composition comprising at least one cyclosporin in admixture with an amount of at least one intermediate molecular weight fatty acid mono- or di-glyceride sufficient to dissolve the cyclosporin.

The invention also provides a method of suppressing the mammalian immune system by administering to a mammal, especially a human being, an oily solution or aqueous emulsion comprising an effective amount of at least one cyclosporin in association with sufficient of at least one intermediate molecular weight fatty acid mono- or di- glyceride to dissolve said cyclosporin.

The invention still further provides a method of treating the ocular symptoms of Behcet's Syndrome by administering to the eye of a mammal, especially a human being, a composition, preferably in the form of an oily solution or aqueous emulsion, comprising an effective amount of at least one cyclosporin in association with sufficient of at least one intermediate molecular weight fatty acid mono- or di- glyceride to dissolve said cyclosporin.

DETAILED DESCRIPTION OF THE INVENTION

As currently commercially available, cyclosporin is supplied as a mixture in which the principal ingredient is cyclosporin A and which also contains a certain, but much smaller, quantity of the other cyclosporins, specifically cyclosporins B, C, D and G. However, as already explained, the present invention can be applied either to a pure cyclosporin (whether cyclosporin A or another member of the cyclosporin group) or to a mixture of individual cyclosporins, such as the above-mentioned commercial mixture.

The effectiveness of the intermediate molecular weight fatty acid mono- and di- glycerides is rather unexpected in view of the disadvantages associated with the use of other closely related compounds.

Thus, higher fatty acid glyceride preparations are defective because of the reasons given above. On the other hand, lower fatty acid glycerides are ill-tasting and smell offensive, and, as these glycerides are naturally soluble in water, a mixed solvent of water and a lower fatty acid glyceride can hardly be expected to dissolve cyclosporin. Moreover, comparing the various intermediate fatty acid glycerides with each other, the triglycerides show a significantly lower ability to dissolve the cyclosporins and thus disperse them in water.

On the contrary, an oily preparation composed of an intermediate molecular weight fatty acid mono- or di-glyceride and cyclosporin has the advantages of being capable of containing a high concentration of cyclosporin, of being emulsified easily with water in the absence of a surface active agent or in the presence of a highly safe (i.e. weakly emulsifying) surface active agent, and of having a high stability on standing.

There is no particular restriction on the nature of the intermediate molecular weight fatty acid mono- or di-glyceride used in the present invention, and any mono- or di- glyceride of an intermediate molecular weight fatty acid having from 6 to 10 carbon atoms may be used. Examples of preferred intermediate molecular weight fatty acids include: caproic acid, 4-methyl-pentanoic acid, enanthic acid, 5-methylhexanoic acid, 2-ethylhexanoic acid, caprylic acid (more properly named "octanoic acid"), 6-methylheptanoic acid, pelargonic acid, capric acid and 8-methylnonanoic acid. The more preferred fatty acids contain from 8 to 10 carbon atoms, most preferably 8 carbon atoms.

Thus, the mono- and di- glycerides of fatty acids containing 8 carbon atoms are still more preferred, and the diglycerides of fatty acids containing 8 carbon atoms are most preferred.

Because there are three positions on the glycerin molecule to which the fatty acid residues may attach, mono- and di- glycerides can exist in the form of symmetric $\beta$-monoglycerides and $\alpha,\alpha'$-diglycerides as well as asymmetric $\alpha$-monoglycerides and $\alpha,\beta$-diglycerides. The present invention embraces the use of all of these glycerides, and the exact nature of these isomers and whether a single such compound or a mixture of such compounds is employed is not critical to the invention.

Also, in the case of the diglycerides, the fatty acid residues may be the same as each other, or they may be mixed diglycerides in which there are two different kinds of fatty acid residues. The present invention embraces the use of all of these glycerides.

It is also possible to use a single one of these intermediate molecular weight fatty acid mono- or di- glycerides or to use a mixture of any two or more thereof.

The amount of the intermediate molecular weight fatty acid mono- or di- glyceride employed in this invention is not particularly restricted, and this amount may vary, depending on the kind of intermediate molecular weight fatty acid mono- or di- glyceride employed and the kind of formulation employed. For example, because of the strong emulsifiability of mono- and di- glycerides, an oily preparation containing only cyclosporin and at least one mono- and/or di- glyceride can be administered at a concentration of nearly 100% because it will change to an almost completely emulsified state in vivo.

However, in general, it is preferred to use the composition of the present invention in the form of an emulsion in the presence of water. In this case, the non-aqueous components are preferably present in amounts of about 50% by weight or less, more preferably about 25% or less, of the whole composition. If the preparation is to be applied topically, the non-aqueous components are preferably present in an amount of 1% by weight or less.

The weight ratio of the intermediate molecular weight fatty acid mono- and/or di- glycerides to the cyclosporin used in this invention is preferably from 1:0.1 to 1:1, more preferably from 1:0.1 to 1:0.5, and most preferably from 1:0.25 to 1:0.5.

If the preparation takes the form of an emulsion, a surface active agent may also be employed, if desired, in order to improve the stability on standing of the emulsion and the absorption in vivo of the active agent, by decreasing the sizes of the oil particles. Preferred examples of the surface active agents which may be employed include: polyoxyethylene-polyoxypropylene glycol; and phospholipids, such as lecithin. However, there is no particular restriction on the nature of any such added surface active agent, provided that it is highly safe.

It is also possible in accordance with the present invention to use an intermediate molecular weight fatty acid mono- or di- glyceride in admixture with any other vegetable oil, or to improve the preparation containing these basic substances by adding conventional additives, such as a pH adjuster, an osmotic pressure adjuster, an antiseptic, a surface active agent, a perfume or a corrigent.

The composition of the present invention may be provided in the form of an oily solution of the cyclosporin and the intermediate molecular weight fatty acid mono- or di- qlyceride together with a suitable vehicle, or in the form of an aqueous emulsion thereof. It is also possible to provide the composition as a powdery product by spray-drying or freeze-drying such an emulsion.

The oily solution and aqueous emulsion preparations of the present invention can be employed for oral administration or for administration by injection; they can also be applied to the eye without any trouble. The powdery product can not only be employed for oral administration, for injection or for application to the eye by dissolving it before use, but it can also be used as the material for oral solid preparations, such as powders, granules, capsules and tablets, and for suppositories.

In the case of an oily solution or aqueous emulsion, the concentration of cyclosporin is preferably from 0.1 to 500 mg/ml, and more preferably from 0.2 to 200 mg/ml.

The compositions of the invention will, of course, be formulated in conventional pharmaceutical forms appropriate to the intended route of administration, for example as formulations for oral administration or for topical administration, especially to the eyes. However, appropriate formulations are well known in the art and require no further explanation here.

The invention is further illustrated by the following Examples, Test Examples and Experiments. In the following, all parts and percentages are by weight. The cyclosporin samples used in the Examples, Test Examples and Experiments were supplied by Sandoz Ltd., Switzerland. The commercially available "Sandimmune" (Trade name) contains the same kind of cyclosporin compound as was used in these Examples. Test Examples and Experiments.

TEST EXAMPLE 1

Emulsifiability

The mixed triglyceride of caprylic acid and capric acid (Trade name: ODO; obtainable from The Nisshin Oil Mills, Ltd.), castor oil, olive oil and peanut oil were examined for emulsifiability.

The emulsion was composed of 10 weight % or 20 weight % of the glyceride, 0 weight %, 1.2 weight % or 2 weight % of a surface active agent (Pluronic F68, a trade name for a material obtainable from Asahi Denka Kogyo K.K. or dipalmitoylphosphatidylcholine obtainable from Nippon Oils & Fats Co., Ltd.). the balance being a physiological saline solution.

Each solution was emulsified by using a Physcotron emulsifier (a trade name for an emulsifier obtainable from Niti-on Irika Kikai Co., Ltd.), and the condition of each emulsion was judged by the naked eye. Judging from the separation between oil and water, the mixed triglyceride of caprylic acid and capric acid was found to be the best among the 4 kinds of glycerides, regardless of the compositions, and a great difference could be observed between the emulsifiability of this and the emulsifiability of castor oil, olive oil or peanut oil. Although the mixed triglyceride of caprylic acid and capric acid is not included in this invention, even this intermediate molecular weight fatty acid triglyceride was found to exhibit far better emulsifiability than did any of the higher fatty acid glycerides.

TEST EXAMPLE 2

Emulsifiability 1 ml of an intermediate molecular weight fatty acid glyceride and 9 ml of water were placed in a test tube, and the test tube was shaken lightly to examine the emulsifiability of the intermediate molecular weight fatty acid glyceride.

The intermediate molecular weight fatty acid glycerides examined in this Example were caprylic acid mono-, di- and tri- glycerides and caproic acid diglyceride.

Caprylic acid monoglyceride was emulsified in a manner very close to self-emulsification. There was little separation between oil and water and the emulsion was very stable.

Caprylic acid triglyceride was emulsified only after vigorous shaking by hand, but the emulsion tended to separate into oil and water after it had been allowed to stand for some time.

Caproic acid diglyceride and caprylic acid diglyceride both showed an intermediate emulsifiability between the two mentioned above.

In short, good emulsifiability was observed in the following order: caprylic acid monoglyceride, caproic acid diglyceride, caprylic acid diglyceride and caprylic acid triglyceride.

TEST EXAMPLE 3

Solubility

Table 2 below shows the solubility of cyclosporin in each of the glycerides at room temperature.

TABLE 2

| Glyceride | Solubility [mg/ml] |
| --- | --- |
| Peanut oil | 50 |
| Olive oil | 10 |
| Soybean oil | 20 |
| Castor oil | 250 |
| Mixed triglyceride of caprylic acid and lauric acid (trade name Miglyol 812, Huls Troisdorf A.G.) | 50 |
| Mixed triglyceride of caprylic acid and capric acid (trade name ODO, The Nisshin Oil Mills, Ltd.) | 50 |
| Caprylic acid diglyceride (trade name Sunfat GDC, Taiyo Kagaku Co., Ltd.) | 520 |
| Caprylic acid monoglyceride (The Nisshin Oil Mills, Ltd.) | 550 |
| Caproic acid diglyceride (Nikko Chemical Co., Ltd.) | 510 |

TEST EXAMPLE 4

Solubility

The solubility of cyclosporin in four kinds of glycerides at 45° C. is shown in Table 3 below.

TABLE 3

| Glycerides | Solubility [mg/ml] |
| --- | --- |
| mixed triglyceride of caprylic acid and capric acid (Trade name: ODO; The Nisshin Oil Mills, Ltd.) | 130 |
| Lauric acid monoglyceride (Trade name: Sunsoft 757; Taiyo Kagaku Co., Ltd.) | 300 |
| Oleic acid monoglyceride (Trade name: MGO; Nikko Chemical Co., Ltd.) | 400 |
| Capric acid monoglyceride (Trade name: Sunsoft 767; Taiyo Kagaku Co., Ltd.) | 600 |

From the results reported above in Test Examples 3 and 4, it can be seen that the solubility of cyclosporin in intermediate molecular weight fatty acid glycerides (in which the fatty acid contains from 6 to 10 carbon atoms) was particularly high in the mono- and di- glycerides, as compared with the higher fatty acid glycerides and the intermediate molecular weight triglycerides.

EXAMPLE 1

An emulsion containing cyclosporin was prepared. It was composed of one part of cyclosporin, 2 parts of caprylic acid diglyceride (Trade name: Sunfat GDC), 1 part of Pluronic F68 and 96 parts of physiological saline solution, a total of 100 parts. Two kinds of solutions, one in which cyclosporin was dissolved in Sunfat GDC, and the other in which Pluronic F68 was dissolved in the physiological saline solution, were mixed together and emulsified by ultrasonic treatment. The size of the oil particles in the resulting emulsion was not larger than 1 μm. No separation of cyclosporin could be observed.

EXAMPLE 2

An emulsion containing cyclosporin was prepared. It was composed of 2 parts of cyclosporin, 5 parts of caprylic acid diglyceride (Trade name: Sunfat GDC), 1.2 parts of soy lecithin (Trade name: Lecinol S-10EX; Nikko Chemicals Co., Ltd.) and 91.8 parts of physiological saline solution, a total of 100 parts. Two kinds of solutions, one in which cyclosporin was dissolved in Sunfat GDC, and the other in which soy lecithin was mixed with the physiological saline solution, were mixed together, and emulsified by ultrasonic treatment.

The resulting emulsion was slightly viscous and the size of the oil particles was not larger than 1 μm. No separation of cyclosporin could be observed.

EXAMPLE 3

An emulsion containing cyclosporin was prepared. It was composed of 0.1 part of cyclosporin, 0.25 part of caprylic acid diglyceride (Trade name: Sunfat GDC), 2 parts of Pluronic F68 and 97.65 parts of physiological saline solution, a total of 100 parts. Two kinds of solutions, one in which cyclosporin was dissolved in Sunfat GDC, and the other in which Pluronic F68 was dissolved in the physiological saline solution, were mixed together and treated 5 times using a laboratory homogenizer [Manton-Gaulin 15M-8TA (Gaulin Corporation)-]at 300 kg/cm$^2$. The size of the oil particles was not larger than 1 μm.

EXAMPLE 4

An emulsion containing cyclosporin was prepared. It was composed of 5 parts of cyclosporin, 10 parts of caprylic acid diglyceride (Trade name: Sunfat GDC), 1 part of Pluronic F68 and 84 parts of purified water, a total of 100 parts. Two kinds of solutions, one in which cyclosporin was dissolved in Sunfat GDC, and the other in which Pluronic F68 was dissolved in purified water, were mixed together, and emulsified by ultrasonic treatment. The resulting emulsion was slightly viscous, and the size of oil particle was not larger than 1 μm.

EXAMPLE 5

Following the procedures described in Examples 1, 2, 3 and 4. Similar emulsions were obtained from caproic acid diglyceride and caprylic acid monoglyceride after similar treatment. The results were very similar.

EXPERIMENT 1

The emulsion preparation prepared as described in Example 3 was applied to the right eye of a male Japanese white rabbit 10 times at intervals of 30 minutes, and at a dose of 0.05 ml each time. Thirty minutes after the final application, the tissue was exised. At the time of obtaining the corneal sample, the corneal epidermis was removed in order· to obtain such a sample as free as possible from cyclosporin adsorbed on the surface. The mean cyclosporin levels in the tissues of three eye samples were 3400 ng/ml and 700 ng/ml for the corneal parenchyma and for the ciliary body respectively. Therefore, the transfer of cyclosporin into the eye tissue was established. Cyclosporin was analyzed quantitatively using a radio-immunoassay kit (Sandoz Ltd.)

EXPERIMENT 2

The emulsion prepared in Example 4 or Sandimmun Drink Solution (Sandoz Pharmaceutical Co. Ltd.& Sankyo Co., Ltd., which was used as control and which is available commercially), each containing cyclosporin, was administered orally at a dose of 10 mg/kg (calculated as cyclosporin) to a Beagle dog which had been previously fasted. Blood samples were taken at the times shown in Table 4 below to determine the blood cyclosporin levels, using a radioimmunoassay kit (Sandoz Ltd.).

TABLE 4

| Time after administration | Blood cyclosporin level [ng/ml] (the mean value from 2 dogs) | | | | | | |
|---|---|---|---|---|---|---|---|
| | 0 | 1 | 2 | 3 | 4 | 6 | 24 hours |
| Sample | | | | | | | |
| Sandimmun Drink Solution | <30 | <30 | 310 | 310 | 280 | 180 | 40 |
| Emulsion of Example 4 | <30 | 210 | 370 | 580 | 480 | 350 | 40 |

It was demonstrated that the emulsion of this invention brought about good absorbability compared with the control.

As will be appreciated from the foregoing description and, in particular, the above Examples illustrating the present invention, the specific teachings of the present invention enable the preparation of pharmaceutical compositions comprising cyclosporins in solution in selected mono- and di- glycerides, which are capable of directly forming aqueous emulsions, as well as pharmaceutical compositions comprising such aqueous emulsions, without any need for any additional co-solvent component for the cyclosporin, e.g. without the need for the addition of ethanol or of any other solubiliser for the cyclosporin.

In a particular aspect, the present invention also provides: a pharmaceutical composition in accordance with the invention, e.g. as herein described, claimed or exemplified, which is free or substantially free from ethanol and/or from any trans-esterification product of a vegetable oil (whether natural or hydrogenated) tri-glyceride and a polyalkylene polyol.

Preferably the compositions in accordance with this aspect of the present invention are free or substantially free from any further solubiliser or co-solubiliser for the cyclosporin.

We claim:

1. A pharmaceutical composition comprising at least one cyclosporin in admixture with an amount of at least one mono- or di- glyceride of a $C_6$–$C_{10}$ fatty acid sufficient to dissolve the cyclosporin.

2. The composition of claim 1, wherein said fatty acid has from 8 to 10 carbon atoms.

3. The composition of claim 1, wherein said fatty acid has 8 carbon atoms.

4. The composition of claim 1, wherein said fatty acid is at least one acid selected from the group consisting of caproic acid, 4-methylpentanoic acid, enanthic acid, 5-methylhexanoic acid, 2-ethylhexanoic acid, caprylic acid, 6-methylheptanoic acid, pelargonic acid, capric acid and 8-methylnonanoic acid.

5. The composition of claim 1, wherein said fatty acid is at least one acid selected from the group consisting of caproic acid, caprylic acid and capric acid.

6. The composition of claim 1, wherein said glyceride is a diglyceride.

7. The composition of claim 2, wherein said glyceride is a diglyceride.

8. The composition of claim 3, wherein said glyceride is a diglyceride.

9. The composition of claim 4, wherein said glyceride is a diglyceride.

10. The composition of claim 1, wherein the weight ratio of the glyceride to the cyclosporin is from 1:0.1 to 1:1.

11. The composition of claim 1, wherein the weight ratio of the glyceride to the cyclosporin is from 1:0.1 to 1:0.5.

12. The composition of claim 1, wherein the weight ratio of the glyceride to the cyclosporin is from 1:0.25 to 1:0.5.

13. A pharmaceutical composition comprising an oily solution or aqueous emulsion of at least one cyclosporin in admixture with an amount of at least one mono- or di- glyceride of a $C_6$–$C_{10}$ fatty acid sufficient to dissolve the cyclosporin.

14. The composition of claim 13, wherein said fatty acid has from 8 to 10 carbon atoms.

15. The composition of claim 13, wherein said fatty acid has 8 carbon atoms.

16. The composition of claim 13, wherein said fatty acid is at least one acid selected from the group consisting of caproic acid, 4-methylpentanoic acid, enanthic acid, 5-methylhexanoic acid, 2-ethylhexanoic acid, caprylic acid, 6-methylheptanoic acid pelargonic acid, capric acid and 8-methylnonanoic acid.

17. The composition of claim 13, wherein said fatty acid is at least one acid selected from the group consisting of caproic acid, caprylic acid and capric acid.

18. The composition of claim 13, wherein said glyceride is a diglyceride.

19. The composition of claim 14, wherein said glyceride is a diglyceride.

20. The composition of claim 15, wherein said glyceride is a diglyceride.

21. The composition of claim 16, wherein said glyceride is a diglyceride.

22. The composition of claim 13, wherein the weight ratio of the glyceride to the cyclosporin is from 1:0.1 to 1:1.

23. The composition of claim 13, wherein the weight ratio of the glyceride to the cyclosporin is from 1:0.1 to 1:0.5.

24. The composition of claim 13, wherein the weight ratio of the glyceride to the cyclosporin is from 1:0.25 to 1:0.5.

25. The composition of claim 13, wherein the concentration of cyclosporin is from 0.1 to 500 mg/ml.

26. The composition of claim 25, wherein said concentration is from 0.2 to 200 mg/ml.

27. The composition of claim 13, wherein non-aqueous components are present in amounts of about 50% by weight or less of the whole composition.

28. The composition of claim 13, wherein non-aqueous components are present in amounts of about 25% or less of the whole composition.

29. A method of suppressing the mammalian immune system by administering to a mammal an oily solution or aqueous emulsion comprising an effective amount of at least one cyclosporin in association with sufficient of at least one mono- or di- glyceride of a $C_6$–$C_{10}$ fatty acid to dissolve said cyclosporin.

30. The method of claim 29, wherein said fatty acid has 8 carbon atoms.

31. The method of claim 29, wherein said fatty acid is at least one acid selected from the group consisting of caproic acid, caprylic acid and capric acid.

32. The method of claim 31, wherein said glyceride is a diglyceride.

33. The method of claim 29, wherein the weight ratio of the glyceride to the cyclosporin is from 1:0.1 to 1:1.

34. The method of claim 29, wherein the pharmaceutical composition is employed in the form of an oily solution or aqueous emulsion.

35. The method of claim 34, wherein the concentration of cyclosporin is from 0.1 to 500 mg/ml.

36. The method of claim 34, wherein non-aqueous components are present in amounts of about 50% by weight or less of the whole composition.

37. A method of treating the ocular symptoms of Behcet's Syndrome by administering to the eye of a mammal a composition comprising an effective amount of at least one cyclosporin in association with sufficient of at least one mono- or di- glyceride of a $C_6$–$C_{10}$ fatty acid to dissolve said cyclosporin.

38. The method of claim 37, wherein said fatty acid is at least one acid selected from the group consisting of caproic acid, caprylic acid and capric acid.

39. The method of claim 38, wherein said glyceride is a diglyceride.

40. The method of claim 37, wherein the weight ratio of the glyceride to the cyclosporin is from 1:0.1 to 1:1.

41. The method of claim 37, wherein the pharmaceutical composition is employed in the form of an oily solution or aqueous emulsion.

42. The method of claim 41, wherein the concentration of cyclosporin is from 0.1 to 500 mg/ml.

43. The method of claim 41, wherein non-aqueous components are present in amounts of about 50% by weight or less of the whole composition.

44. A pharmaceutical composition in the form of a non-irritating oily solution or aqueous emulsion and comprising at least one cyclosporin in admixture with an amount of at least one mono- or di- glyceride of a $C_6$–$C_{10}$ fatty acid sufficient to dissolve the cyclosporin.

45. The composition of claim 44, wherein said fatty acid is at least one acid selected from the group consisting of caproic acid, caprylic acid and capric acid.

46. The composition of claim 44, wherein said glyceride is a diglyceride.

47. A pharmaceutical composition in the form of a non-irritating oily solution or aqueous emulsion and comprising at least one cyclosporin of which a major proportion is cyclosporin A in admixture with an amount of at least one mono- or di- glyceride of a $C_6$–$C_{10}$ fatty acid sufficient to dissolve the cyclosporin.

48. The composition of claim 47, wherein said fatty acid is at least one acid selected from the group consisting of caproic acid, caprylic acid and capric acid.

49. The composition of claim 47, wherein said glyceride is a diglyceride.

50. A method of suppressing the mammalian immune system by the oral administration to a mammal of a composition comprising an effective amount of at least one cyclosporin in association with sufficient of at least one mono- or di- glyceride of a $C_6$–$C_{10}$ fatty acid to dissolve said cyclosporin.

51. The method of claim 50, wherein said fatty acid has 8 carbon atoms.

52. The method of claim 50, wherein said fatty acid is at least one acid selected from the group consisting of caproic acid, caprylic acid and capric acid.

53. The method of claim 52, wherein said glyceride is a diglyceride.

54. The method of claim 50, wherein the weight ratio of the glyceride to the cyclosporin is from 1:0.1 to 1:1.

55. The method of claim 50, wherein the pharmaceutical composition is employed in the form of an oily solution or aqueous emulsion.

56. The method of claim 55, wherein the concentration of cyclosporin is from 0.1 to 500 mg/ml.

57. The method of claim 55, wherein non-aqueous components are present in amounts of about 50% by weight or less of the whole composition.

58. A pharmaceutical composition in which a solution of at least one cyclosporin in an amount of at least one mono- or di- glyceride of a $C_6$–$C_{10}$ fatty acid sufficient to dissolve the cyclosporin is emulsified in an aqueous medium.

* * * * *